United States Patent [19]
Chen et al.

[11] Patent Number: 5,728,854
[45] Date of Patent: Mar. 17, 1998

[54] METHOD FOR SEPARATING IRON FROM NICKEL AND/OR CADMIUM FROM A WASTE CONTAINING THE SAME

[75] Inventors: Ching-Chyi Chen; Fong-Ru Yang, both of Hsinchu, Taiwan

[73] Assignee: Industrial Technology Research Institute, Hsinchu, Taiwan

[21] Appl. No.: 693,348

[22] Filed: Aug. 6, 1996

[51] Int. Cl.$^6$ .................... C07F 15/02; C07F 15/04
[52] U.S. Cl. .................... 556/149; 423/138; 423/140
[58] Field of Search .................... 556/149; 423/138, 423/140

[56] References Cited

U.S. PATENT DOCUMENTS

| | | | |
|---|---|---|---|
| 3,637,776 | 1/1972 | Welsh | 556/149 |
| 4,228,091 | 10/1980 | Partenheimer | 423/140 |
| 4,401,463 | 8/1983 | Melin et al. | |
| 5,407,463 | 4/1995 | Van Erkel | |

FOREIGN PATENT DOCUMENTS

| | | | |
|---|---|---|---|
| 2260497 | 6/1973 | Germany | 556/149 |
| 934969 | 8/1963 | United Kingdom | 556/149 |

OTHER PUBLICATIONS

Zhihuai Xue et al., "Separation and Recovery of Nickel and Cadmium from Spent Cd–Ni Storage Batteries and Their Process Wastes", *Separation Science and Technology*, 27(2), 1992, pp.213–221.

*Primary Examiner*—Wayne Langel
*Attorney, Agent, or Firm*—Bacon & Thomas

[57] ABSTRACT

A method for separating iron for nickel and/or cadmium contained in a battery waste is composed of a first step in which the spent batteries are crushed and calcined. The calcined pieces are mixed with an acetic acid aqueous solution before acetic acid and water are removed by evaporation or distillation so as to produce a residue containing metallic acetates. Water, the residue and an oxidant are mixed such that $Fe^+$ and $Fe^{++}$ acetates are converted into a basic ferric acetate, $Fe(CH_3COO)_2OH$, which is insoluble in water and is recovered by filtration.

20 Claims, 4 Drawing Sheets

5,728,854

1

METHOD FOR SEPARATING IRON FROM NICKEL AND/OR CADMIUM FROM A WASTE CONTAINING THE SAME

FIELD OF THE INVENTION

The present invention relates generally to a method for separating iron from nickel and/or cadmium, and more particularly to a method for separating iron from nickel and cadmium from a battery waste containing such iron, nickel and cadmium.

BACKGROUND OF THE INVENTION

The nickel-cadmium batteries are widely used in consumer goods, such as portable radio, shaver, toy, flashlight, etc., as well as in various industries as the power source for locomotive, electric car, air-conditioning system, hospitals, high-rise buildings, aircraft, and so forth.

It is therefore readily apparent that the ubiquitous applications of the nickel-cadmium batteries have become sources of environmental pollution, with the culprit being that the cadmium contained in the battery is a potential pollutant of water and soil if the spent nickel-cadmium batteries are not properly disposed of.

There are various methods for separation and recovery of nickel and cadmium from the spent nickel-cadmium batteries. The method disclosed in the U.S. Pat. No. 4,401,463 is a case in point. The method involve pyrolysis, which is made to occur by raising the temperature inside the furnace from about 100° C. to an initial temperature of about 400° C. or 500° C. The vaporization of the cadmium takes place at about 900° C. in the presence of a reducing protective gas. The cadmium vapor is then condensed to form the liquid cadmium, which is cast into the cadmium rods. Such a pyrolysis process described above is relatively simple in operation; nevertheless it is limited in design in that it must be provided with a special control means for preventing the pollution caused by the cadmium vapor, and that it can not be used to dispose of the spent nickel-iron battery or the spent nickel-hydrogen battery.

Zhihuai Xue, et al. disclose a method for separation and recovery of nickel and cadmium from a waste containing such nickel and cadmium. The method is described in their article entitled "SEPARATION AND RECOVERY OF NICKEL AND CADMIUM FROM SPENT Cd-Ni STORAGE BATTERIES AND THEIR PROCESS WASTES", which was published in Separation Science and Technology, 27(2), 1992, pp. 213–221. The method involves a process in which the spent Cd-Ni batteries are treated at a high temperature of 600° C. for one hour for incinerating the organic substances contained in the batteries. The roasted sludge so obtained is then treated in sequence with sulfuric acid and ammonia to form cadmium and nickel ammonia complexes, which are then treated with a series of reactions to form cadmium carbonate and nickel hydroxide. Such a prior art method as described above is defective in design in that it is rather complicated, and that it is not cost-effective.

The U.S. Pat. No. 5,407,463 discloses an extraction method for separating and recovering cadmium and nickel from batteries. The method involves a first step in which the spent batteries are crashed to pieces. The pieces having a linear size smaller than 2.8 mm are leached with a strong acid at 90° C. The cadmium is then removed from the leaching liquid with the aid of an extractant TBP (tributyl phosphate). The cadmium extraction rate is as high as 99.5%. The metallic cadmium and the metallic nickel are obtained by electrolysis. The method is not cost-effective in view of the fact that it involves a tedious process in which iron ions must be removed repeatedly from the organic phase and aqueous phase of the extraction.

In short, the methods for separating and recovering cadmium and nickel from the spent batteries can be generalized as the pyrolysis process and the wet process, with the former being relatively simple as compared with the latter. The pyrolysis process has disadvantages in that it does not yield the high-value intermediate products, and that it produces the toxic cadmium vapor, and further that it is not applicable to the nickel-iron battery and the nickel-hydrogen battery. On the other hand, the hydrolysis process yields the high-value intermediate product, such as cadmium carbonate, and can be used to separate and recover the nickel-iron battery and the nickel-hydrogen battery. However, the wet process has its own share of shortcoming of being inefficient in view of the fact that the iron ions must be removed repeatedly in the process. Moreover, the iron component is not recovered as a useful material in both the hydrolysis process and the wet process.

SUMMARY OF THE INVENTION

The primary objective of the present invention is to provide an improved method for separating iron from nickel and/or cadmium contained in a spent battery waste.

The secondary objective of the present invention is to provide a method for separating iron oxide from a mixture containing iron oxide and nickel oxide and/or cadmium oxide.

In keeping with the principle of the present invention, the foregoing objectives of the present invention are attained by a method for separating iron from nickel and/or cadmium contained in a waste. The method comprises a first step in which the metallic components contained in the waste are converted into the metallic oxides by calcining the waste in the presence of oxygen. The calcined products so obtained are mixed with an aqueous solution of acetic acid such that substantially all the metallic oxides are converted into metallic salts of acetic acid. A residue of the metallic salts of acetic acid is formed by evaporating or distilling the solution. The residue so obtained is then mixed with water so that the metallic salts of acetic acid is dissolved in water. The metallic salts of acetic acid that can be dissolved in water include $Fe^+$ and $Fe^{++}$ salts, and nickel and/or cadmium salts. While mixing with said water or thereafter, an oxidant is added to convert $Fe^+$ and $Fe^{++}$ salts into $Fe(CH_3COO)_2OH$ which is precipitated and then removed from the mixture by a solid-liquid separation method.

The method of the present invention for separating and recovering iron oxide from a mixture containing iron oxide and nickel oxide and/or cadmium oxide comprises the step in which an aqueous solution of acetic acid is added to said mixture such that the metallic oxides are converted to metallic salts of acetic acid. The resulting solution is then separated from the mixture, and a residue is formed by evaporating or distilling the solution. Water is again added to the residue to dissolve the metallic salts of acetic acid which include $Fe^+$ and $Fe^{++}$ salts, and nickel and/or cadmium salts. While addition of said water or thereafter, an oxidant is added so as to convert $Fe^+$ and $Fe^{++}$ salts into $Fe(CH_3COO)_2OH$, which is precipitated and then removed from the mixture by a solid-liquid separation.

The method of the present invention is characterized in that an acetic acid aqueous solution is used to dissolve oxides of iron, nickel and cadmium, and an oxidant is used to convert water soluble $Fe^+$ and $Fe^{++}$ salts of acetic acid into water insoluble $Fe(CH_3COO)_2OH$. The removal of iron is as high as 95%. On the other hand, the $Fe(CH_3COO)_2OH$ is soluble in pure acetic acid. For this reason, the acetic acid must be removed from the acetic acid aqueous solution containing the $Fe^+$ and $Fe^{++}$, nickel and cadmium salts of acetic acid prior to converting the water soluble $Fe^+$ and $Fe^{++}$ salts of acetic acid into the water insoluble $Fe(CH_3COO)_2OH$ which can be separated from the water soluble nickel and cadmium salts of acetic acid. The acetic acid can exist in the pure form with an concentration of 100%. As a result, the acetic acid removed in the method of the present invention is recycled to minimize the pollution problem.

Preferably, the pH of the resulting mixture by adding said water is adjusted to remain ≧ about 5 by adding an alkali at the time when or after the oxidant is added.

Preferably, the acetic acid removed in the method of the present invention by evaporation or distillation is recycled to form the acetic acid component of the aqueous solution of acetic acid used in the method of the present invention described above.

The metallic components contained in the waste referred to in the method of the present invention may include iron and nickel. The metallic salts of acetic acid which can be dissolved in water include $Fe^+$, $Fe^{++}$ and nickel salts of acetic acid.

The metallic components contained in the waste referred to in the method of the present invention may include iron and cadmium. The metallic salts of acetic acid which can be dissolved in water include $Fe^+$, $Fe^{++}$ and cadmium salts of acetic acid.

The metallic components contained in the waste referred to in the method of the present invention include iron, nickel and cadmium. The metallic salts of acetic acid which can be dissolved in water include $Fe^+$, $Fe^{++}$, nickel and cadmium salts of acetic acid.

The waste referred to in the method of the present invention may further contain one or more metallic components whose acetates are water soluble, such as zinc, copper, lead, strontium, zirconium and silver.

In the methods of the present invention, said aqueous solution of acetic acid is preferably mixed with the waste and the mixture of metallic oxides by mechanically agitation with the assistance of bubbling air into the mixture.

DETAILED DESCRIPTION OF THE EMBODIMENTS

Figure 1:
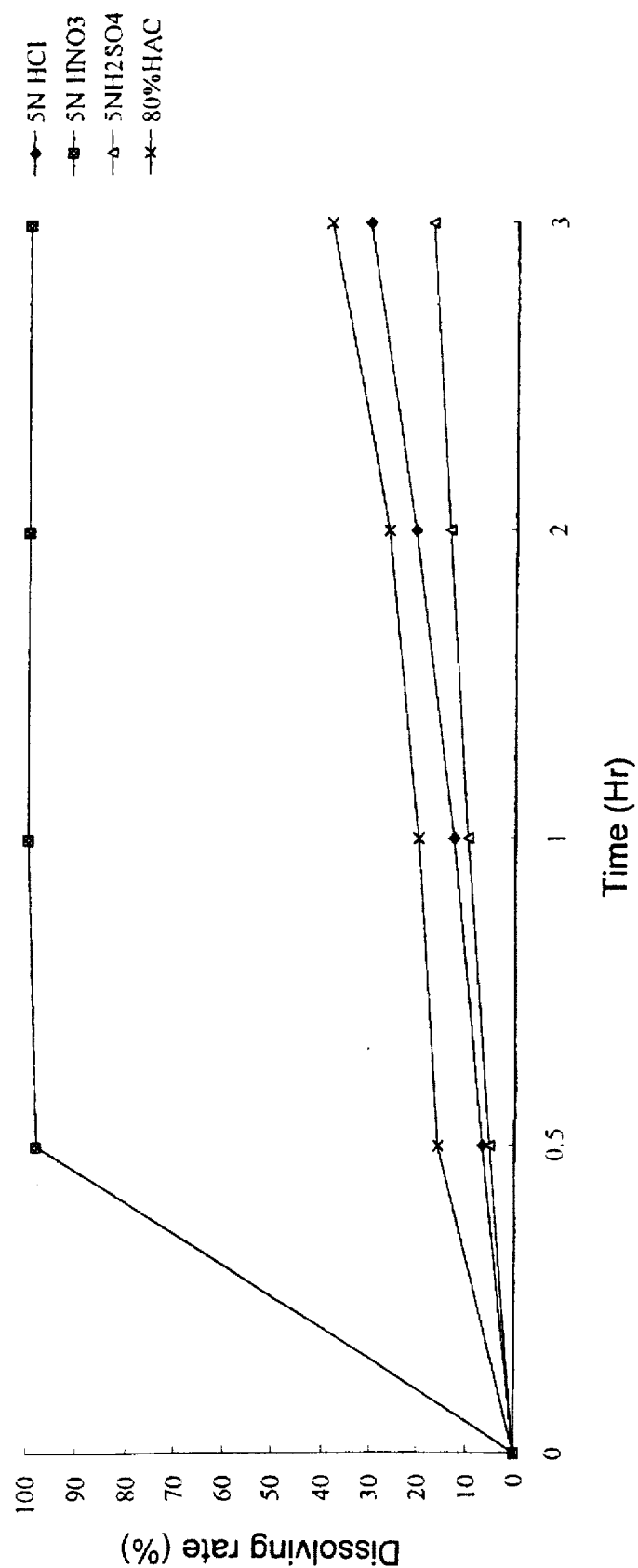
FIG. 1 shows the dissolving rates of the nickel-cadmium battery electrode plates by various acids, including 80% HAC (—x—), 5N HCL (—♦—), 5N $HNO_3$(—■—), and 5N $H_2SO_4$(—Δ—).

The method of the present invention for separating iron from nickel and cadmium from spent nickel-cadmium batteries comprises the steps of (1) crushing and sieving; (2) incinerating and calcining; (3) dissolving by acetic acid; (4) distilling under a reduced pressure; (5) dissolving by adding water; and (6) vacuum filtration.

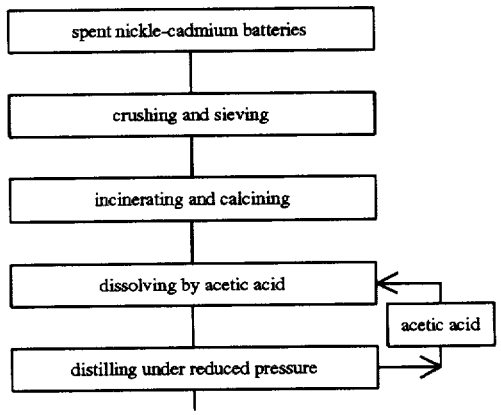

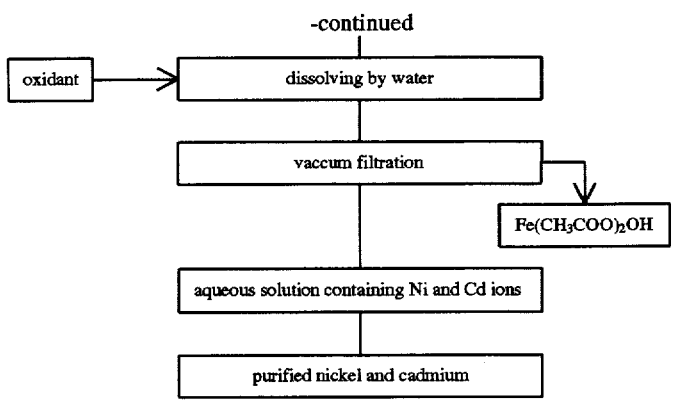

On the basis of the forms of the electrode plates of a nickel-cadmium battery, the nickel-cadmium battery can be classified as a tubular type, a bag type, and a sintering type. The cohesive force of the active material to the positive electrode plate and the negative electrode plate is weak while the volume variations of active material during charging and the discharging are great, thereby resulting in an increase in the inner resistance. In order to give an added strength to the electrodes, the nickel-cadmium batteries of the early age are of the tubular type or the bag type for filling with the electrode plate active material. The modern nickel-cadmium batteries are provided with the electrode plates of the sintering type. The main reaction of the nickel-cadmium battery are:

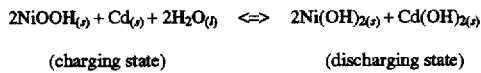

(charging state)　　　　　(discharging state)

The product at the nickel electrode in the charging state is NiOOH, and is Ni(OH)$_2$ in the discharging state. The product at the cadmium electrode in the charging state is Cd, and is Cd(OH)$_2$ in the discharging state. KOH of the electrolyte is not directly involved in the reaction. The materials in the above-mentioned states may exist when a battery is spent. As far as structure is concerned, the electrode plates of the sintering type has a base plate of porous nickel plate. The positive and the negative electrodes are respectively electroplated with the active materials of nickel and cadmium. The active material of the negative electrode contains 20% iron. The partition between the electrodes is made of a porous PVC material. The battery housing and the battery cap are made of a steel material electroplated with nickel, or made of polystyrene. The composition of a typical nickel-cadmium battery is shown in Table 1.

TABLE 1 composition of a typical nickel-cadmium battery (wt %)

| Type | Ni | Cd | Steel/ plastic/graphite | Electrolyte* |
|---|---|---|---|---|
| small size closed type | 20–30 | 11–15 | 35–40 | 30 |
| large size open type | 10 | 8 | 49 | 33 |

*weight of water contained in electrolyte

The crushing and sieving process involves the use of a crushing machine in which the small-sized and closed battery (or the dismantled electrode plate of a large-sized industrial battery) is crushed to pieces having a size smaller than 5 mm to facilitate the incinerating and calcining process as well as the acetic acid dissolving process. Generally speaking, the crushed pieces contain larger pieces of the plastic material or the steel material electroplated with nickel, and smaller pieces of the electrode active material.

The incinerating and calcining process is brought about at a high temperature in the presence of sufficient oxygen in a furnace, so as to burn out the plastic material and to oxidize the electrode plate. The high temperature referred to above is in a range of 500°–600° C. The process lasts for a period of about two hours.

The incinerated and calcined fragments are dissolved in an acetic acid aqueous solution such that the metallic oxides brought about by the calcining are converted into acetate compounds. The concentration of the acetic acid aqueous solution ranges between 50% and 100%, preferably 80%. The dissolving process is brought about at a temperature ranging between the room temperature and the boiling point of the acetic acid aqueous solution, preferably at 90° C. The dissolving rate is accelerated at a higher concentration of the acetic acid aqueous and a higher dissolving temperature. The acceleration of the dissolving rate can also be attained by an addition of other acid, such as nitric acid, to the acetic acid aqueous solution. However, the iron removal percentage of the method of the present invention is undermined by the addition of other acid to the acetic acid aqueous solution.

Acetic acid is a weak organic acid capable of dissolving nickel, cadmium and iron in the form of oxide or metallic salts of other acid, such as nitric acid.

The dissolving process is preferably brought about by agitating the mixture of said acetic acid aqueous solution and the incinerated and calcined fragments constantly and introducing air into the mixture so as to enable the metallic oxides to react fully with acetic acid. The oxygen of air serves to facilitate the conversion of Fe$^+$ and Fe$^{++}$ salts of acetic acid into Fe(CH$_3$COO)$_2$OH, and thus enhance the dissolving of the iron oxide.

As shown in FIG. 1, the dissolving rate of the calcined fragments of the electrode plate by 5N nitric acid is the fastest while the dissolving rates by acetic acid (80%), HCl (5N), and H$_2$SO$_4$ (5N) are similar to one another. The experiments were done with the predetermined weight of the calcined fragments of the electrode plates of the large-size batteries, which were dissolved at 90° C. in aqueous acid solutions which were ten times of the weight of the crushed pieces.

Figure 2:
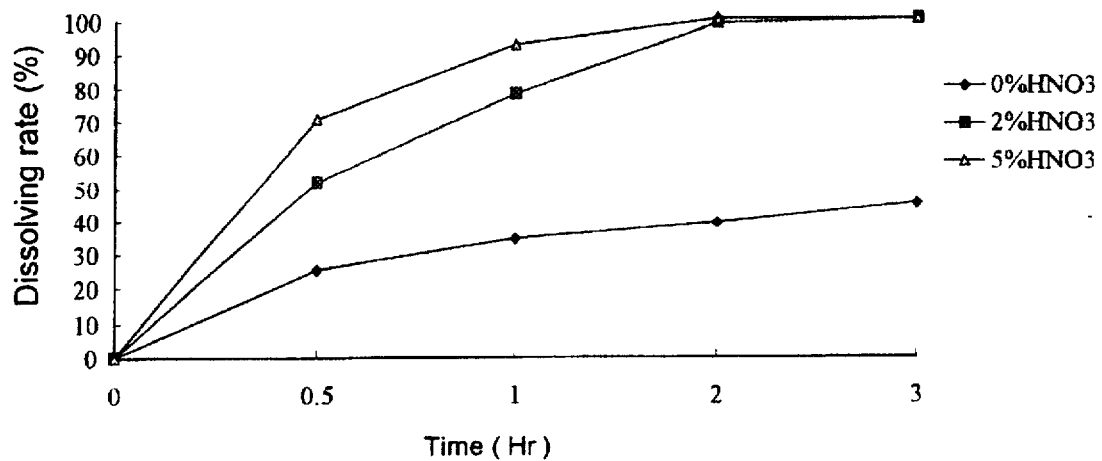
FIG. 2 shows the effect on the dissolving rate of the nickel-cadmium battery electrode plates by 80% acetic acid aqueous solution containing 0% (—♦—), 2% (—■—) and 5% (—Δ—) of $HNO_3$.

As shown in FIG. 2, the calcined fragments of the electrode plates were completely dissolved in about two hours by an 80% acetic acid aqueous solution to which 2 or 5% of nitric acid were added. The experiments were carried out with the calcined fragments of the electrode plates of the large-size batteries, which were dissolved at 90° C. in acetic acid aqueous solutions (80%) to which various amounts of nitric acid (0%, 2%, 5%) were added.

Figure 3:
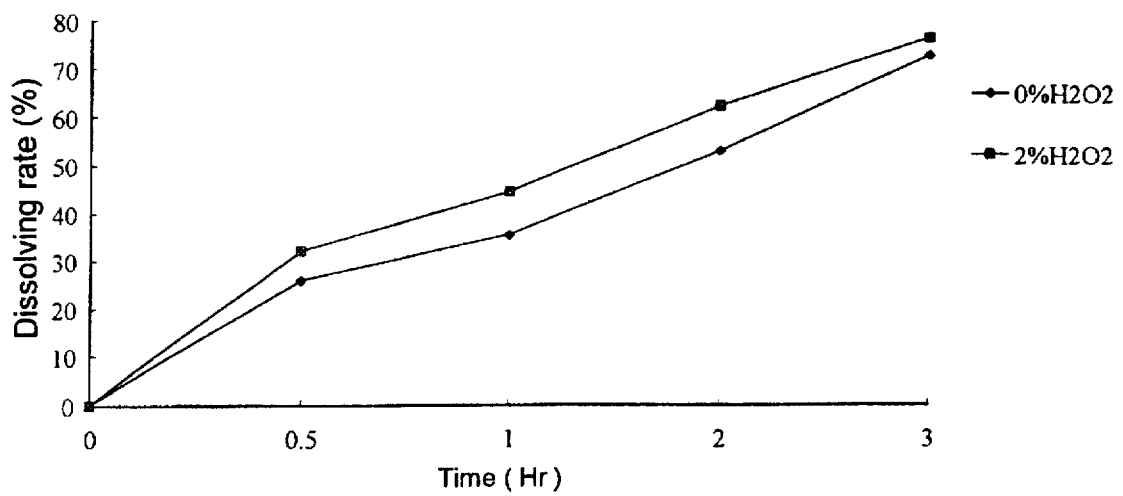
FIG. 3 shows the effect on the dissolving rate of the calcined nickel-cadmium battery by 80% acetic acid aqueous solutions containing 0% (—♦—) and 2% (—■—) of hydrogen peroxide.

As shown in FIG. 3, the dissolving rate of the calcined small-size nickel-cadmium battery is improved when an oxidant is added. The experiments were done with the calcined fragments of the small-size nickel-cadmium battery, which were dissolved at 90° C. in acetic acid solutions (80%) which were ten times of the weight of the calcined fragments, and to which various amounts of hydrogen peroxide (0%, 2%) were added.

The extra acetic acid and water contained in the mixture of the acetic acid aqueous solution and the incinerated and calcined fragments of the dissolving process were removed by the distilling process which was carried out under a reduced pressure. The recovered acetic acid was used again as the source of acetic acid of the acetic acid aqueous solution. The pressure referred to above ranges between the normal pressure and 1 mm Hg or less, preferably 20 mm Hg. The distilling temperature was adjusted in conjunction with the pressure. The temperature may range between the room temperature and the boiling point, depending on the applied pressure.

The residue of the acetate compounds so obtained in the distilling process is treated with water such that the acetate compounds of $Fe^+$, $Fe^{++}$, nickel and cadmium are fully dissolved in water, and that the soluble acetate compounds of $Fe^+$ and $Fe^{++}$ are converted into insoluble $Fe(CH_3COO)_2OH$, so as to facilitate the separation of iron from the nickel and cadmium.

The oxides of nickel, cadmium and iron are converted via acetic acid into the corresponding acetate compounds, including $Ni(CH_3COO)_2$, $Cd(CH_3COO)_2$, $Fe(CH_3COO)$, $Fe(CH_3COO)_2$, $Fe(CH_3COO)_2OH$. The residue contains these acetate compounds, in which only the $Fe(CH_3COO)_2OH$ is water insoluble.

The equilibrium equation of $Fe(CH_3COO)_{2(aq)}$ and $Fe(CH_3COO)_2OH_{(s)}$ in water is as follows:

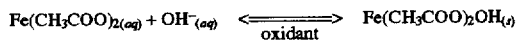

On the basis of the above equation, it is clear that an increase in [OH⁻] concentration will shift the equilibrium point toward the right side so that enhances the formation of the precipitate of $Fe(CH_3COO)_2OH_{(s)}$. As a result, the removal of the iron ions from the aqueous solution is aided by the addition of the oxidant and an alkali.

TABLE 2

| properties of related products of the present invention | | | |
|---|---|---|---|
| Product | Chemical formula | Properties | Uses |
| Nickel Acetate | Ni(CH₃COO)₂ (containing 4 moles of crystal water) | *green crystal *soluble in water, acid and alcohol | *textile dyeing agent *catalyst |
| Cadmium Acetate | Cd(CH₃COO)₂ (containing 3 moles of crystal water) | *colorless crystal *soluble in water, acid and alcohol | *textile dyeing aids *ceramic glazing agent *agent for electroplating |
| Ferric Acetate Basic | Fe(CH₃COO)₂OH | *red powder *insoluble in water, soluble in | *textile dyeing and printing aids *wood preservative |

TABLE 2-continued

| properties of related products of the present invention | | | |
|---|---|---|---|
| Product | Chemical formula | Properties | Uses |
| Ferrous Acetate | Fe(CH₃COO)₂ (containing 4 moles of crystal water) | acid and alcohol *green crystal *soluble in water, acid and alcohol | *leather dyestuff *textile dyeing and printing aids *wood preservative *leather dyestuff |

Figure 4:
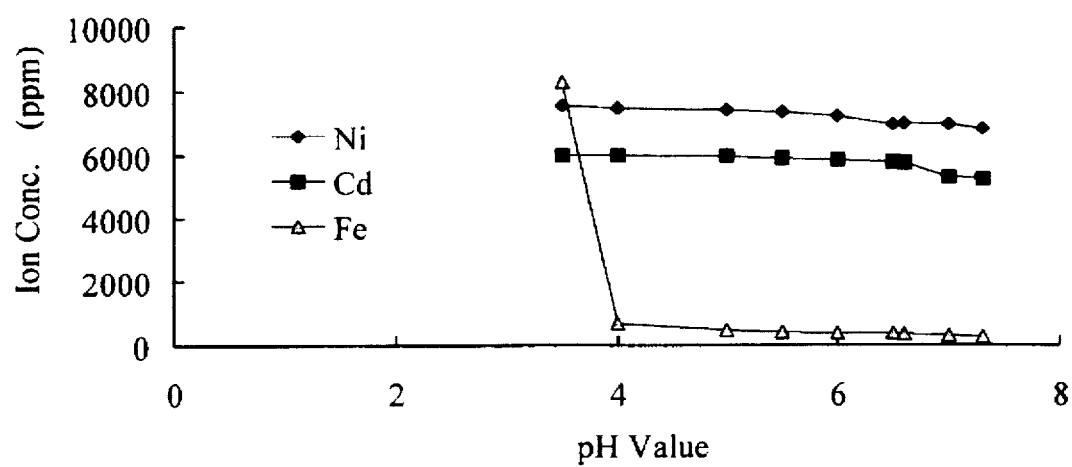
FIG. 4 shows the concentrations of $Cd^{++}$, $Ni^{++}$ and $Fe^{++}$ ions in the resulting solution by adding said water to said residue in the present method, in which the pH value of the solution is varied by adding an alkali thereto.
Figure 5:
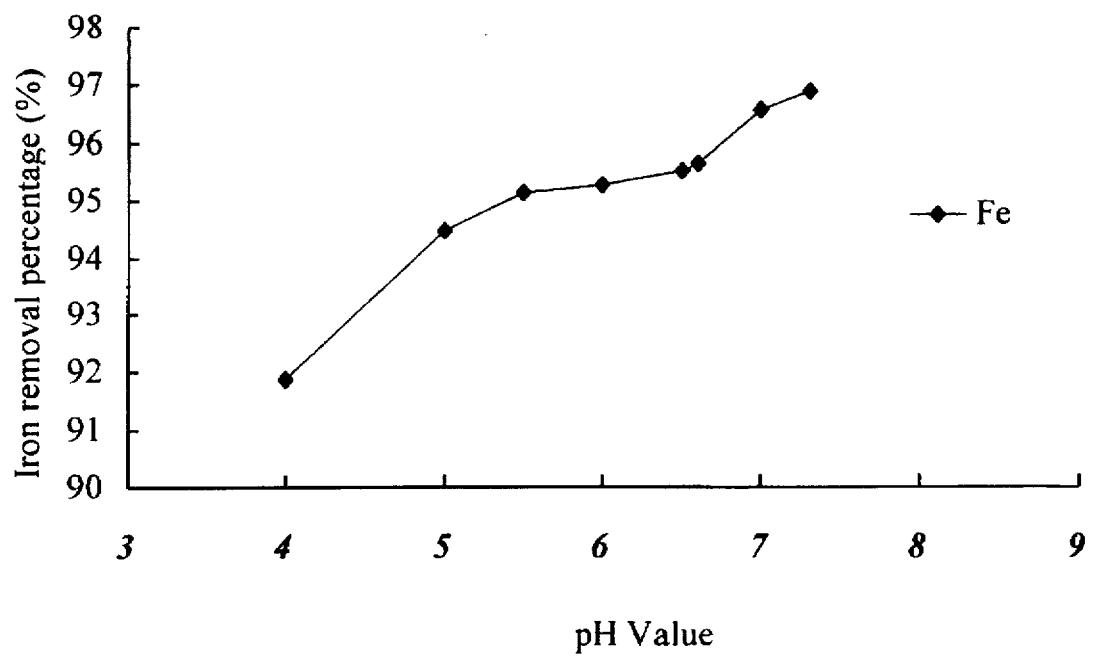
FIG. 5 shows the iron removal percentages of the present method at various pH values of the resulting solutions by adding said water and optionally alkali to said residue.

As shown in FIGS. 4 and 5, a substantial reduction in the $Fe^{++}$ ions contained in the aqueous solution which is formed by adding said water to said residue is brought about when the pH value of the aqueous solution is greater than 5, thereby indicating that the removal percentage of iron is as high as 95%. The adjustment of various pH values of the aqueous solution may be attained by addition of NaOH solution.

The vacuum filtration of the aqueous solution containing the $Fe(CH_3COO)_2OH_{(s)}$ is achieved by filtering the mixture with a filter paper or a microporous material, in which the mixture is poured on one side of the filter paper and the pressure of another side thereof is reduced to accelerate the filtration. The vacuum filtration process is capable of separating the soluble acetate compounds of nickel and cadmium from the $Fe(CH_3COO)_2OH$ precipitate. The pressure reduced in the vacuum filtration process ranges between the normal pressure and 1 mm Hg or less, preferably 20 mm Hg. The mixture to be filtered was first heated at a temperature ranging between the room temperature and the boiling point of the solution of the mixture, preferably 60° C.

Upon completion of the filtration process, $Ni(CH_3COO)_{2(aq)}$ and $Cd(CH_3COO)_{2(aq)}$ contained in the filtrate were separated by the electrolytic winning, the organic solvent extraction, or the selective precipitation of cadmium carbonate.

The present invention will be more readily understood upon a thoughtful deliberation of the following detailed description of an embodiment, which is to be regarded in all respects as being merely illustrative and not restrictive. Unless it is indicated otherwise, the percentage referred to in the embodiment is based on weight.

EMBODIMENT

Ten small-size nickel-cadmium batteries were crushed with a metal crushing machine into pieces having a size smaller than 5 mm. The pieces were rinsed and dried before they were incinerated and calcined at 600° C. under atmosphere for two hours. Upon being cooled, 50 grams of the pieces were mixed with 500 ml of 80% acetic acid aqueous solution. The mixture was agitated constantly at 90° C. while bubbling air into the mixture for 12 hours, so as to bring about the dissolving reaction of acetic acid. The solution so obtained was found to contain the ions of Ni 29.0 g/l, Cd 16.6 g/l and Fe 30.2 g/l and was distilled under the pressure of 20 mm Hg so as to remove the acid and water from the solution and obtain a residue. During the distillation, caution was taken to avoid any hot points having a temperature >120° C. Thereafter, 500 ml of 2% hydrogen peroxide aqueous solution was added to dissolve the residue and to oxidize the resulting acetate compounds of $Fe^+$ and $Fe^{++}$, in which the reaction mixture was maintained at 60° C. for one hour. The pH of the solution of the reaction mixture was adjusted to 7.0 by means of adding NaOH aqueous solution, and then the reaction mixture was subjected to a vacuum filtration treatment at 60° C. The filtrate so obtained was light green in color and composed mainly of the dissociated nickel and cadmium acetate compounds, with the metal ion contents being Ni 28.6 g/l, Cd 16.1 g/l, Fe 1.0 g/l. The removal percentage of iron was calculated to be 96.7%. The filtered precipitate was red in color and was basic ferric acetate, $Fe(CH_3COO)_2OH$, and the purity of basic ferric acetate was about 98% after it was rinsed with a weak alkaline solution containing 1% of hydrogen peroxide for removing nickel and cadmium ions attached to the surface of the basic ferric acetate.

What is claimed is:

1. A method for separating iron from nickel and/or cadmium which are contained in a waste, said method comprising the steps of:
   (a) calcining said waste in the presence of oxygen so as to convert all metals contained in said waste into metal oxides;
   (b) mixing said metal oxides with an acetic acid aqueous solution containing said acetic acid in a quantity sufficient to convert substantially all the metal oxides into metallic salts of acetic acid;
   (c) removing said acetic acid and water from the resulting mixture of said step (b) by evaporation or distillation so as to produce a residue containing said metallic salts of acetic acid;
   (d) dissolving said residue with water to form an aqueous solution containing water soluble metallic salts of acetic acid of said metallic salts of acetic acid including $Fe^+$ acetate, $Fe^{++}$ acetate and nickel acetate and/or cadmium acetate;
   (e) adding an oxidant to said aqueous solution of step (d) when or after said residue was dissolved with said water so as to convert said $Fe^+$ acetate and $Fe^{++}$ acetate into a water insoluble basic ferric acetate, $Fe(CH_3COO)_2OH$; and
   (f) recovering said basic ferric acetate from the resulting mixture of step (e) by a solid-liquid separation means.

2. The method as defined in claim 1, wherein an alkali is added during or after said oxidant is added to said aqueous solution in step (e) such that said aqueous solution has a pH value equal to or greater than 5.

3. The method as defined in claim 1, wherein said acetic acid aqueous solution of step (b) has an acetic acid concentration ranging between 50% and 100%; and wherein said metal oxides are mixed with said acetic acid aqueous solution at a temperature ranging between a room temperature and a boiling point of said acetic acid aqueous solution.

4. The method as defined in claim 1, wherein said waste is calcined at a temperature ranging between 500° C. and 600° C.

5. The method as defined in claim 1, wherein said oxidant referred to in step (e) is oxygen or hydrogen peroxide.

6. The method as defined in claim 1, wherein said oxidant of step (e) and said water of step (d) are mixed simultaneously with said residue.

7. The method as defined in claim 2, wherein said oxidant of step (e) and said alkali are added simultaneously to said aqueous solution of step (d).

8. The method as defined in claim 1, wherein said acetic acid removed in said step (c) is recycled such that said acetic acid is used to form said acetic acid aqueous solution of step (b).

9. The method as defined in claim 6, wherein, prior to step (f), an alkali is added to the resulting mixture of step (e) so as to adjust a pH value of the resulting mixture of step (e) being greater than or equal to 5.

10. The method as defined in claim 1, wherein said metals contained in said waste of step (a) consist essentially of iron and nickel; and said water soluble metallic salts of acetic acid in said step (d) include $Fe^+$ acetate, $Fe^{++}$ acetate and nickel acetate.

11. The method as defined in claim 1, wherein said metals contained in said waste of step (a) consist essentially of iron and cadmium; and said water soluble metallic salts of acetic acid in said step (d) include $Fe^+$ acetate, $Fe^{++}$ acetate and cadmium acetate.

12. The method as defined in claim 1, wherein said metals contained in said waste of step (a) consist essentially of iron, nickel and cadmium; and said water soluble metallic salts of acetic acid in said step (d) include $Fe^+$ acetate, $Fe^{++}$ acetate, nickel acetate and cadmium acetate.

13. The method as defined in claim 1, wherein said waste further contains one or more metallic components selected from a group consisting of zinc, copper, lead, strontium, zirconium, and silver.

14. The method as defined in claim 3, wherein said acetic acid aqueous solution of said step (b) has an acetic acid concentration of 80%; and said acetic acid aqueous solution is mixed with said metal oxides at 90° C.

15. The method as defined in claim 1, wherein said metal oxides and said acetic acid aqueous solution are mixed and agitated with air being introduced into the mixture simultaneously.

16. The method as defined in claim 1, wherein said solid-liquid separation means referred to in step (f) is a filtration means.

17. A method for separating iron oxide from a mixture containing iron oxide and nickel oxide and/or cadmium oxide, said method comprising the steps of:
   (A) mixing said mixture with an acetic acid aqueous solution containing said acetic acid in a quantity sufficient to convert substantially all metallic oxides contained in said mixture into metallic acetates;
   (B) removing said acetic acid and water from the resulting mixture of said step (a) by evaporation or distillation so as to produce a residue containing said metallic acetates;
   (C) dissolving said residue with water to form an aqueous solution containing water soluble metallic acetates of said metallic acetates including $Fe^+$ acetate, $Fe^{++}$ acetate and nickel acetate and/or cadmium acetate;
   (D) adding an oxidant to said aqueous solution of step (C) when or after said residue was dissolved with said water so as to convert said $Fe^+$ acetate and $Fe^{++}$ acetate into a water insoluble basic ferric acetate, $Fe(CH_3COO)_2OH$; and
   (E) recovering said basic ferric acetate from the resulting mixture of step (D) by a solid-liquid separation means.

18. The method as defined in claim 17, wherein an alkali is added during or after said oxidant is added to said aqueous solution in step (D) such that said aqueous solution has a pH value equal to or greater than 5.

19. The method as defined in claim 17, wherein said acetic acid aqueous solution of step (A) has an acetic acid concentration ranging between 50% and 100%; and said acetic acid aqueous solution and said mixture are mixed at a temperature ranging between a room temperature and a boiling point of said acetic acid aqueous solution.

20. The method as defined in claim 17, wherein said mixture and said acetic acid aqueous solution of said step (A) are mixed and stirred with air being introduced into the mixture simultaneously.

* * * * *